US00PP09264P

United States Patent [19]

Chamberlain

[11] Patent Number: Plant 9,264

[45] Date of Patent: Aug. 29, 1995

[54] NECTARINE TREE—'SCARLET SUN' CULTIVAR

[75] Inventor: Thomas O. Chamberlain, Visalia, Calif.

[73] Assignee: Metropolitan Life Insurance Company, Del Ray, Calif.

[21] Appl. No.: 352,869

[22] Filed: Dec. 2, 1994

[51] Int. Cl.[6] ..... A01H 5/00

[52] U.S. Cl. ..... Plt./41.3

[58] Field of Search ..... Plt. 41.1, 41.3

*Primary Examiner*—James R. Feyrer

*Attorney, Agent, or Firm*—Burns, Doane, Swecker & Mathis

[57] ABSTRACT

A new and distinct cultivar of nectarine tree is provided that is named Scarlet Sun. The new cultivar originated from an open-pollinated peach seed of unknown parentage that was planted by the originator when seeking to develop new peach and nectarine cultivars of commercial potential primarily for California growing conditions. The new variety produces large freestone fruit with a high degree of bright red skin coloration. The harvest time is relatively early and commonly provides a crop suitable for commercial harvest from about June 15th to 25th when grown in central San Joaquin Valley of California near Fresno. The new cultivar offers improvements in fruit quality, color, and size over other freestone nectarine cultivars maturing at approximately the same time. For instance, the new cultivar is proposed as a superior alternative to the Sunfre nectarine cultivar (non-patented in the United States) that currently is harvested in approximately the same season when grown in the stone-fruit production areas of Washington State.

1 Drawing Sheet

SUMMARY OF THE INVENTION

The present invention is directed to a new and distinct nectarine cultivar that originated as a chance seedling in the nursery of H. P. Metzler & Sons, Inc. located at the corner of Del Rey and Jefferson Avenues in Del Rey, Calif. It was the goal of the originator to discover and select new peach and nectarine cultivars from populations of open-pollinated seedlings that are particularly suited for commercial use under California growing conditions. In the pursuit of this goal the originator routinely grew out open-pollinated seed collected in bearing orchards of successful peach and nectarine commercial cultivars.

Available records indicate that the seed that resulted in the formation of the new cultivar of the present invention is believed to have been collected during the winter of 1979 from Row No. 32 of an otherwise undesignated block of peach and nectarine trees growing in the same nursery of H. P. Metzler & Sons, Inc. Further information concerning the origin of the seed is not available, and the parentage of the new cultivar of the present invention is unknown.

The fruit of the new nectarine cultivar of the present invention was first observed during June, 1981, and its distinctiveness was preliminarily ascertained by originator. Had the originator not planted, discovered and preserved the original tree of the new cultivar it would have been lost to mankind.

It was found that the new nectarine tree of the present invention:

(a) forms attractive early-maturing fruit having a generally uniformly large size wherein approximately 75 to 90 percent of the skin is bright red in coloration.

(b) forms firm, crisp, highly-flavored yellow freestone flesh of excellent quality having a small amount of red tinging, and (c) exhibits a spreading and slightly upright growth habit.

Historically higher prices commonly are received by growers who are able to supply quality fruit to the early-season flesh fruit market. Accordingly, new cultivars that are able to meet this need are in great demand. It generally is recognized to be difficult with existing varieties for growers to produce nectarines of a large size early in the harvest season because of the relatively short time in which to achieve maturity.

The new cultivar is capable of producing a quality nectarine harvest having a large fruit size that matures early in the harvest season. For instance, when grown at Del Rey, Calif., fruit maturity dates of approximately June 15th to 25th commonly are observed, and when grown near Maryhill, Wash., fruit maturity dates of July 15th to 25th commonly are observed.

The previously available Sunfre nectarine cultivar (non-patent in the United States) is a public release from the USDA and commonly is grown in the stone fruit production areas of Washington State. The new cultivar of the present invention is being proposed as a superior alternative for growers of the Sunfre cultivar that commonly is harvested in approximately the same season. For instance, the Sunfre cultivar is recognized to be deficient in size, color, and finish under some growing conditions. A test planting that includes the Sunfre cultivar and the new cultivar of the present invention has shown that the fruit of the new cultivar ripens approximately three to five days later than the Sunfre cultivar, has a larger fruit size, has a greater degree of red coloration, and possesses a better finish on a reliable basis. The fruit flesh of the new cultivar possesses low acidity. The fruit skin tenaciously adheres to the flesh.

Under the direction of the originator, the new cultivar was first asexually propagated in the spring of 1982 by budding onto Nemaguard peach seedlings, by technicians at the Del Rey, Calif. growing area of H. P.

Metzler & Sons, Inc. Additionally, in 1985, wood from the original tree was top-grafted onto an existing scion orchard of Agri-Sun Nursery at the corner of Clarkson and Temperance Avenues, near Selma, Calif. Through observation over a twelve-year period, the characteristics of the asexually reproduced trees, including both the budded and subsequently top-grafted trees, have proven to be identical to those of the selected nectarine seedling of the present invention.

The new cultivar initially was designated 32-79-14. The new cultivar of the present invention subsequently was named the Scarlet Sun cultivar.

BRIEF DESCRIPTION OF THE PHOTOGRAPH

The accompanying photograph shows specimens of foliage and mature fruit of the new cultivar as depicted in color as nearly true as it is possible to make the same in a color illustration of this type. All specimens were obtained from the first generation top-grafted trees of the Scarlet Sun cultivar growing near the corner of Clarkson and Temperance Avenues, near Selma, Calif. The specimens were harvested on Jun. 20, 1993. At the lower right portion of the photograph the fruit is divided along the suture plane to show the flesh color and freeness of the stone. The photograph was taken on Jun. 24, 1993.

DETAILED DESCRIPTION

The following is a detailed description of the new cultivar that is based upon observation of first generation grafted trees of the new Scarlet Sun cultivar growing at Del Rey, Calif. Color designations are presented while using The R.H.S. Colour Chart of The Royal Horticultural Society, London, England.

TREE

Size: Vigorous.
Growth habit: Spreading and slightly upright.
Productivity: Excellent.
Cropping: Consistent, and heavy.
Trunk:
- *Diameter.*—Medium.
- *Surface texture.*—Normal.
- *Color.*—Grey-Brown Group 199A.
- *Lenticels.*—Erumpant, approximately 10 to 12 per square inch.

Branches:
- *Diameter.*—Medium.
- *Surface texture.*—Normal.
- *Lenticels.*—Erumpant, approximately 12 to 14 per square inch.

Bark: On the current year's growth, the bark at the distal one-third is Yellow-Green Group 144C in coloration. On the sun-exposed surfaces, a red to brownish coloration is evident. This varies from Greyed-Red Group 178C on the new shoots to Greyed-Orange Group 172A on the intermediate portions of the new growth. The basal portions of the current season's growth have rugose, vertically oriented, slightly raised bark netting that is Greyed-Orange Group 165B and Greyed-Orange Group 166B in coloration, randomly dotted with horizontally oriented ovoid-shaped raised lenticels of Greyed-Orange Group 164C. Both the bark netting and the raised lenticels decrease distally in occurrence. The distal one-third commonly is substantially lacking in netting and raised lenticels, and the basal one-third commonly is nearly completely covered with netting and lenticels. On the previous year's growth, the bark is almost completely covered with rugose netting of Greyed-Orange Group 166B, and there are numerous raised medium-sized elliptical lenticels of Greyed-Orange Group 164A with occasional patches of glabrous bark. Old bark on the trunk and limbs is smooth and not shiny, lacks the netting pattern, commonly is Greyed-Orange Group 177A to 177B in coloration and possesses numerous raised medium-sized elliptical lenticels of Greyed-Orange Group 164A.

Leaves:
- *Size.*—Medium.
- *Length.*—Average approximately 4½ inches (11.43 cm) to approximately 4¾ inches (12.07 cm.) on current season's growth.
- *Width.*—Average approximately 1¼ inch (3.18 cm.) to approximately 1½ inch (3.81 cm.) on current season's growth.
- *Shape.*—Lanceolate.
- *Marginal form.*—Simply serrate and occasionally compoundly serrate.
- *Color.*—*Upper; Yellow-Green Group* 146A. Lower: Yellow-Green Group 146B.
- *Petiole.*—Length: Averages approximately 7/16 inch (1.11 cm.). Width: Averages approximately 1/16 inch (0.16 cm.).
- *Glands.*—Small, commonly varying from opposite to alternate on either side of the petiole.
- *Shape.*—Reniform.

Dormant flower buds:
- *Size.*—Small.
- *Diameter.*—Approximately 5/16 inch (0.79 cm.).
- *Length.*—Approximately ⅜ inch (0.95 cm.).
- *Shape.*—Round, and slightly elongated.

Flowers:
- *Date of bloom.*—Approximately March 2nd to 6th at Del Rey, Calif.
- *Size.*—Large.
- *Type.*—Showy.
- *Petals.*—Average approximately 1 inch (2.54 cm.). in length and approximately ¾ inch (1.91 cm.) in width at anthesis.
- *Color.*—Outer edge of the petal commonly is Red-Purple Group 62C and the center and the base of the petal commonly is Red-Purple Group 62A.

FRUIT

Maturity: Normally ready for commercial harvest in the central San Joaquin Valley at Del Rey, Calif. from June 15th to 25th.

Size: Uniformly large.
- *Axial diameter.*—Approximately 2¾ inches (6.99 cm.) to approximately 3 inches (7.62 cm.).
- *Transverse diameter in suture plane.*—Approximately 2¾ inches (6.99 cm.) to approximately 3 inches (7.62 cm.).
- *Transverse diameter at right angle to suture plane.*—Approximately 2½ inches (6.35 cm.) to 2⅞ inches (7.30 cm.).

Form: Uniform and symmetrical. Ovoid to slightly ovate, slightly compressed transversely towards the suture (approximately ¼ inch or 0.64 cm.). Occasionally with slightly unsymmetrical sides (approximately ⅛ inch or 0.32 cm.).
- *Suture.*—Distinct, smooth, and shallow (maximum depression approximately ⅛ inch or 0.32 cm.). Extends from base to apex approximately 4¼ inches (10.80 cm.) with a slightly marked depression on ventral side of the pistil point. Almost entirely inconspicuous on ventral surface.

*Ventral surface.*—Rounded, and non-lipped.

*Stem cavity.*—Flaring, and slightly elongated in suture plane with suture occasionally showing on both sides. Depth: Approximately ½ inch (1.27 cm.). Width in Suture Plane: Approximately ⅞ inch (2.22 cm.). Width at Right Angle to Suture Plane: Approximately ¾ inch (1.91 cm.). Apex: Rounded and mammiform, occasionally cuneate. Base: Rounded to occasionally slightly truncate. Pistil point: Slightly depressed yet apical.

Stem:

*Size.*—Approximately 7/16 inch (1.11 cm.) in length and approximately ⅛ inch (0.32 cm.) in caliper.

*Character.*—Glabrous surface, with strong to medium adherence to the stone.

Skin:

*Surface texture.*—Glabrous with slightly waxy cuticle.

*Adhesion.*—Tenacious to flesh.

*Tendency to crack.*—None.

*Pubescence.*—None.

*Color.*—Over approximately 75 to 90 percent of the skin red, Red Group 46A on darkest most sun-exposed surface of the fruit to Red Group 46B on less exposed surfaces.

*Ground color.*—Yellow-Orange Group 21A.

*Lenticels.*—Inconspicuous, and occasionally slightly conspicuous near basal end.

Flesh:

*Color.*—Yellow-Orange Group 16B with slight red mottling up to approximately ½ way through the flesh from the pit when over-mature, with occasional red mottling of Red Group 46B next to stone on the dorsal side near the base only on highly colored fruits, and commonly scattered red mottling in approximately 10 to 25 percent of the flesh.

*Surface of stone cavity.*—Rough.

*Color of the pit cavity.*—Yellow-Orange Group 16B, and slightly pink in a few areas where red mottling is next to stone.

*Juice.*—Rich, abundant, and mildly acidic.

*Texture.*—Firm and crisp when harvested, meaty, buttery, and melting when eating-ripe.

*Fibers.*—Few, fine, and inconspicuous.

*Ripening.*—Two to three pickings commonly are required from June 15th to 25th at Del Rey, Calif.

*Flavor.*—Mild, low acid, rich, full-flavored, and excellent.

*Aroma.*—Pronounced.

*Eating quality.*—Best.

Stone:

*Type.*—Semi-free from flesh when eating-ripe, adheres slightly to the flesh over the entire surface of the furrows only, and the tops of the ridges commonly are totally free.

*Fibers.*—Medium in length, commonly free on ridges when eating ripe, and commonly clinging in furrows.

*Size.*—Axial length: Approximately 1⅝ inches (4.13 cm.). Transverse width in suture plane: Approximately 1¼ inch (3.18 cm.). Transverse thickness at right angle to suture plane: Approximately ⅞ inch (2.22 cm.).

Form: Variable, and stronly to slightly obovoid and necked.

*Apex.*—Cuneate.

*Base.*—Variable, broad and truncate to nearly oblique.

*Stem adhesion surface.*—Small, round, and approximately ⅛ inch in diameter (0.31 cm.).

*Sides.*—Equal, somewhat flattened toward suture plane, and commonly more broadly curved along the dorsal edge than along the ventral edge.

*Surface.*—Irregularly furrowed toward the apex and the dorsal edge and near ventral edge, and commonly pitted from base to above the center.

*Ridges.*—Ragged ridge apices toward apex of stone and along ventral edge, and rounded ridge apices toward the base of the stone to above the center.

*Pits.*—Mostly elongated, and occasionally circular.

*Dorsal edge.*—Full, with deep, moderately broad groove toward base to above center, commonly with interrupted ridges on either side.

*Ventral edge.*—Moderately thick, with deep, narrow grooves throughout, and slightly winged toward the base.

Use: Commercial fresh market, dessert and culinary.

Keeping quality: Good. Fruit has kept in cold storage from three to four weeks without noticeable deterioration.

Resistance to insects: Comparable to other commercial cultivers grown in arid fruit growing regions of the United States. The performance in humid growing regions has not yet been evaluated.

Resistance to diseases: Comparable to other commercial cultivars grown in arid fruit growing regions of the United States. The performance in humid growing regions has not yet been evaluated.

Shipping quality: Good to excellent dur to firm, crisp flesh and the tenacious adherence of the flesh to skin.

Although the new cultivar of nectarine tree possesses the above-described characteristics as a result of the growing conditions at Del Rey, Calif., it is to be expected that variations of the usual type and magnitude many appear that are caused by differences in growing conditions, fertilization, pruning, pest control and other horticultural practices when the new cultivar is grown in different environments.

I claim:

1. A new and distinct cultivar of nectarine cultivar, having the following combination of characteristics.

(a) forms attractive early-maturing fruit having a generally uniformly large size wherein approximately 75 to 90 percent of the skin is bright red in coloration.

(b) forms firm, crisp, highly-flavored yellow freestone flesh of excellent quality having a small amount of red tinging, and (c) exhibits a spreading and slightly growth habit;

substantially as herein shown and described.

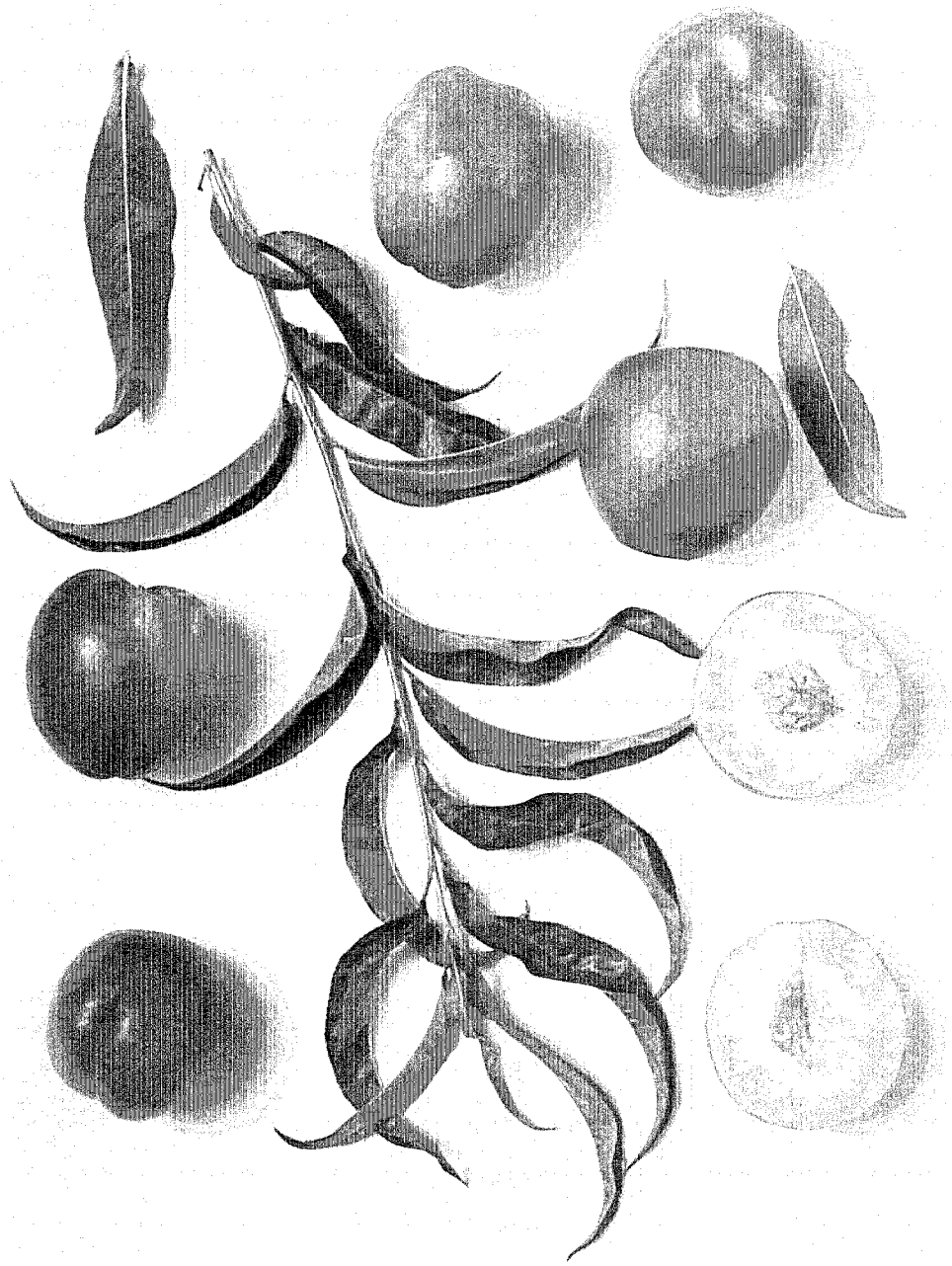

* * * * *